United States Patent [19]

Newberry

[11] 4,095,025

[45] June 13, 1978

[54] 1,3-DIARYL-PYRAZOL-4-ACRYLIC ACID AND DERIVATIVES

[75] Inventor: Robert Anthony Newberry, Bourne End, England

[73] Assignee: John Wyeth & Brother Limited, Maidenhead, England

[21] Appl. No.: 203,458

[22] Filed: Nov. 30, 1971

[30] Foreign Application Priority Data

Dec. 7, 1970 United Kingdom ............... 58051/70

[51] Int. Cl.² .......................................... C07D 231/12
[52] U.S. Cl. ............................... 548/378; 260/295 R; 260/295 AM; 260/295.5 R; 260/295.5 A; 260/296 R; 260/296 D; 424/263; 424/273 P
[58] Field of Search ..................... 260/310 R; 548/378

[56] References Cited

FOREIGN PATENT DOCUMENTS 1,946,370   4/1971   Germany ......................... 260/310 R
   79,086  11/1893   Germany ......................... 260/310 R

OTHER PUBLICATIONS

Nabeya et al. J. Org. Chem. vol. 35, pp. 2015-2021, (1970, Jun., 1970).
Moritani et al. J. Org. Chem. vol. 34, pp. 670-675, (1969).
Bettinetti et al. Gaz. Chim. Ital. vol. 94, pp. 91-108, (1964).
Beilsteins Handbuch der Organischen Chemie 4th ed. vol. 25, pp. 123-124, Berlin, Springer, 1936.
Jones et al. J. Amer. Chem. Soc. vol. 75, p. 4052 relied on, (1953).
Lukes Collection Czechoslov. Chem. Communs. vol. 19, pp. 1205-1214, (1954).

*Primary Examiner*—Natalie Trousof
*Attorney, Agent, or Firm*—Arthur E. Wilfond

[57] ABSTRACT

The invention concerns diarylpyrazole lower alkanoic acids and derivatives which are pharmacologically efficacious as anti-inflammatory agents. The said compounds can be represented by the formula

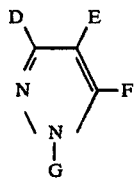

in which one of D, E, F and G represents hydrogen, one is a lower aliphatic acid radical or derivative thereof and the remaining two of D, E, F and G are aryl or heteroaryl radicals.

2 Claims, No Drawings

1,3-DIARYL-PYRAZOL-4-ACRYLIC ACID AND DERIVATIVES

This invention relates to novel heterocyclic aromatic compounds, to processes for the preparation thereof and to pharmaceutical compositions containing such compounds. The heterocyclic aromatic compounds concerned in this invention are pyrazoles substituted by two aryl groups and an aliphatic acid group containing from two to six carbon atoms or a derivative thereof.

The present invention provides compounds of the general formula

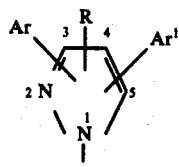
(I)

in which Ar and Ar$^1$ are aryl radicals (which includes in the description below heteroaryl radicals) and which may be the same or different and R is an aliphatic acid radical containing from two to six carbon atoms or a derivative thereof, and the acid addition and quaternary ammonium salts of those compounds in which Ar and/or Ar$^1$ contain a basic substituent.

It is to be understood that each of the radicals Ar, Ar$^1$ and R occupies one of the 1-, 3-, 4- or 5-positions of the pyrazole ring, the remaining position being occupied by a hydrogen atom; thus the invention provides the following twelve structural isomers:

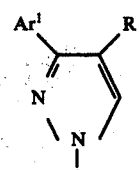
(II)

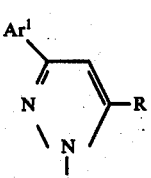
(III)

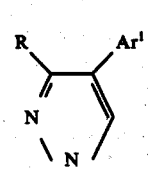
(IV)

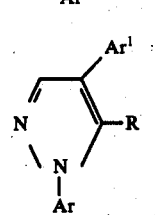
(V)

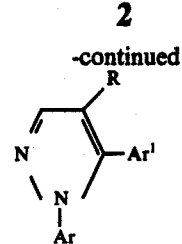
(VI)

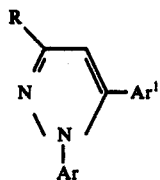
(VII)

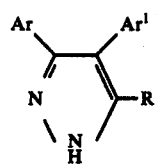
(VIII)

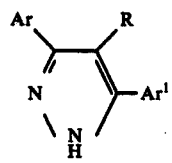
(IX)

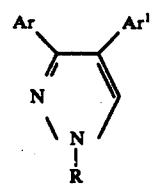
(X)

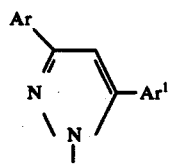
(XI)

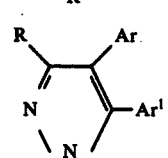
(XII)

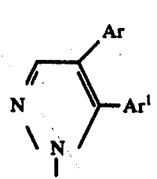
(XIII)

The compounds of the above general formula (I) exhibit pharmacological activity such as anti-inflammatory activity as shown by tests on warm-blooded animals. Some are also intermediates in the preparation of other substituted pyrazoles.

Examples of radicals Ar and Ar$^1$ are phenyl and substituted phenyl. Suitable substituents are halogen (for example fluorine, chlorine or bromine), lower alkyl (for example methyl, ethyl, propyl or butyl), lower alkoxy (for example methoxy, ethoxy, propoxy or butoxy), nitro, amino (including alkyl substituted amino groups) in particular dialkylamino (for example dimethylamino), trifluoromethyl, mercapto, methylthio or methylsulphonyl, as well as 1- and 2- naphthyl, 2- and 3-furyl, 2- and 3-thienyl, 2-, 3- and 4-pyridyl, 2- and 3-indolyl and 2- and 3-pyrrolyl. The radical R preferably is an aliphatic acid radical containing from two to six carbon atoms, more preferably from two to four carbon atoms, or is a suitable derivative thereof, for example an ester, amide, salt or hydroxamic acid derivative thereof. Preferred examples of radicals R are acetic, n-propionic, iso-propionic, and butyric acid radicals as well as ethylenically unsaturated acid radicals, such as acrylic acid. If the acid is in the form of an ester it is preferably the alkyl ester such as the ethyl ester. The alkyl or alkoxy groups preferably contain one to four carbon atoms, but the term "lower" as used herein means the radical contains up to six carbon atoms. One preferred series of compounds are those of general formula (II).

The compounds of general formula (I) may be prepared by first forming a pyrazole of general formula

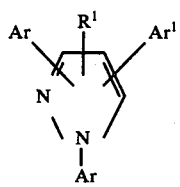 (XIV)

wherein Ar and Ar¹ have the meanings defined above and R¹ is an aliphatic acid radical containing from 2 to 6 carbon atoms or a derivative thereof or is a hydrogen atom or a precursor group for said acid radical or derivative thereof, and in those pyrazoles wherein R¹ does not have the same meanings as R the group R¹ is converted to R by known methods. In addition, one group R may be converted to another group R each within the meanings defined above for R, and if desired an acid addition or quaternary ammonium salt is formed.

The pyrazoles of general formula (XIV) are prepared by methods known in the art, and reference is made to the following publications: Rodd, "Chemistry of Carbon Compounds", Vol. IV (a), Chapter IV, pages 244–260 (1957); Elderfield, "Heterocyclic Compounds", Vol. 5, Chapter 2, pages 45–161 (1957); and Kost and Grandberg in "Advances in Heterocyclic Chemistry", Vol. 6, pages 358–389 (1966). The following reactions are particularly useful in preparing the compounds of formula (XIV):

(A) Cyclisation of one or more compounds appropriately substituted by radicals $R^a$, $R^b$ and $R^c$, wherein $R^a$, $R^b$ and $R^c$ are chosen in any order from Ar, Ar¹, R¹ and hydrogen. Examples of such cyclisations are the following:

(i) Reaction of a hydrazine of formula $R^a$ — NH — NH₂ with (a) a 1,3-dicarbonyl compound of general formulae

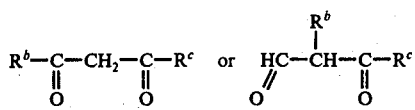

with or without isolation of the intermediate hydrazones of formulae

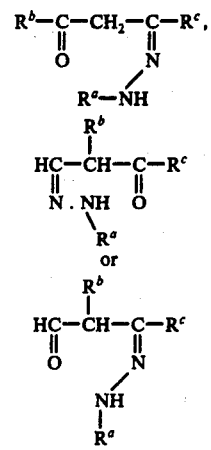

or (b) a halo-alkene of the general formula

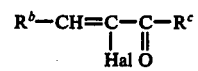

or (c) an acetylene of the general formula

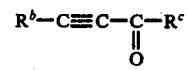

or (d) a carbonyl compound of the general formulae

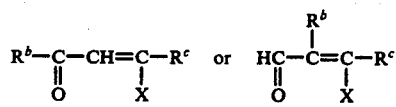

in which X represents a hydroxyl, lower alkoxy, aryl lower alkoxy, acyloxy or disubstituted-amino radical or a halogen atom.

In these reactions the product is a pyrazole of formula

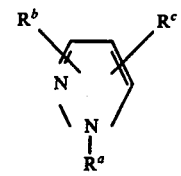

and the radical $R^a$ is preferably chosen from Ar or Ar¹ or is a hydrogen atom, and $R^b$ and $R^c$ are preferably chosen from Ar, Ar¹ or R¹.

(ii) Reaction of an aryldiazonium halide of formula $R^aN_2^+Hal^-$ with a diketo-ester of formula

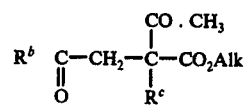

in which Alk is a lower alkyl radical, and $R^c$ represents a hydrogen atom. This reaction is suitable for the preparation of 1,3,5-trisubstituted pyrazoles.

(iii) Reaction of a hydrazone of formula

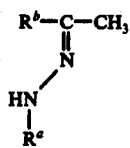

with the adduct formed from phosphoryl chloride and dimethylformamide followed by hydrolysis of the perchlorate of the immonium compound formed to give a pyrazolyl-aldehyde of formula

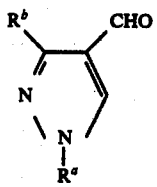

In this reaction, $R^a$ and $R^b$ are chosen from Ar and $Ar^1$ which may be the same or different and have the meanings already defined.

(iv) The reaction of a hydrazone of formula $$R^b - CH = N.NH - R^a$$

with (a) a β-keto-ester of formula

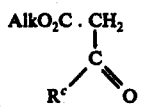

wherein $R^c$ is other than hydrogen
or (b) an acetylene of formula
$$R^c . C \equiv C - COOAlk$$

gives rise to pyrazoles of general formula

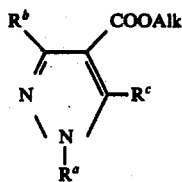

(v) The reaction of an α-halogenohydrazone of general formula

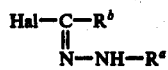

wherein $R^b$ is other than hydrogen with the alkali metal derivatives, e.g. sodio derivatives, of 2-cyanoketones or β-ketonic-esters of formula

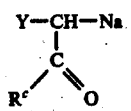

(in which Y is a —CN or —COOAlk radical and $R^c$ is other than hydrogen) gives rise to pyrazoles of general formula

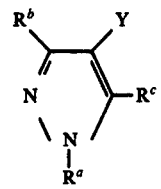

ps (vi) The pyrazoles of general formula (XIV) may also be prepared by reaction of an aliphatic diazo-compound with an acetylene derivative such as a dicarboxylic ester, aldehyde or ketone or nitro derivative. In particular mention must be made of the reaction of diazo compounds of formula $R^a - CHN_2$ with acetylenes of the general formula $$R^b - C \equiv C - R^c$$

to give pyrazoles of formula

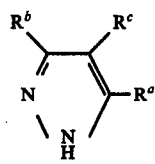

(B) Oxidation of a corresponding pyrazoline with such reagents as bromine, alkali-metal permanganates, alkali-metal ferricyanides, silver nitrate, mercuric oxide, mercuric acetate, lead dioxide and chromic acid, or dehydrogenation with such reagents as sulphur or selenium.

(C) Formation of a pyrazole of formula

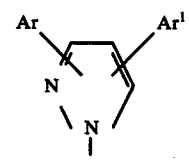

and then introducing the group $R^1$ at the desired position by known methods. For example, it is possible to introduce a halogen atom for example a chlorine, bromine, or iodine atom into the pyrazole ring by treatment with a known suitable halogenating agent. This method is best carried out when a halogen is desired at the 4-position of the ring system. The introduction of a halomethyl group, for example a chloromethyl group, may be carried out by direct halomethylation. Furthermore, if it is desired to prepare a pyrazole containing an acyl or alkyl group at the 4-position, this may be accomplished by subjecting a 4-unsubstituted compound to a Friedel-Crafts reaction. The preparation of a 4-formyl pyrazole is carried out by treating a 4-substituted compound with a mixture of dimethylformamide and phosphoryl chloride. A carboxyl group -COOH can be introduced into a pyrazole containing at least one unsubstituted position by treatment with an organo-lithium compound followed by reaction with carbon dioxide.

When a pyrazole is formed in which the nitrogen atom at the 1-position is unsubstituted, this may be alkylated, arylated or acylated by known methods, to give a compound substituted at the 1-position by the group $R^1$, Ar or $Ar^1$.

Furthermore, when a pyrazole is formed in which $R^1$ does not have the same meaning as R but is a precursor group convertible thereto such as cyanoalkyl, malonic ester, hydroxyalkyl, carboxamidoalkyl, carboalkoxyalkyl, diazoketone, haloalkyl, formyl, carboxy, carboxyalkyl, alkali-metalloalkyl, acrylic acid, halogen, ketone, methyl or hydroxyl residue, then $R^1$ is converted to R by a generally known method such as hydroxamation, (i.e. reaction of an ester group with hydroxylamine to give a hydroxamic acid), esterification, amidation, hydrolysis, alcoholysis, chain extension, oxidation, splitting-off carbon dioxide, reduction, Grignard formation, carbonation and halogenation. In addition one group R may be converted to another group R within its meanings already defined.

When $R^1$ is a precursor of R, it can be reacted with an agent for conversion of the precursor group to R defined as above or a group R can be converted to a different group R as follows:

(i) a haloalkyl group, e.g. a chloromethyl group is reacted with an alkali metal cyanide, e.g. sodium or potassium cyanide and the nitrile obtained is hydrolysed to give a carboxyalkyl or carboxamidoalkyl group R (chain extension and hydrolysis).

(ii) a haloalkyl group is reacted with an alkali metal derivative of a diester such as a malonic acid diester and the product is hydrolysed thereby splitting off carbon dioxide to give a carboxyalkyl group R (chain extension, hydrolysis and splitting off carbon dioxide).

(iii) a —COOH group is reacted with successively (a) a halogenating agent, (b) diazomethane and (c) water or an alcohol, or ammonia or an amine in the presence of a catalyst, e.g. colloidal silver or silver oxide (Arndt - Eistert reaction) to give a carboxyalkyl, carboalkoxyalkyl or carboxamidoalkyl radical R respectively (chain extension).

(iv) an ester, nitrile or amide group is reacted with a hydrolysing agent to give a carboxyalkyl group R (hydrolysis).

(v) an acid group is esterified with an alcohol to give a carboalkoxyalkyl radical R (esterification).

(vi) an ester group is reacted with hydroxylamine to give a hydroxamic acid (hydroxamation).

(vii) an acid group or its salt, e.g. an alkali metal or amine salt is reacted with an acyloxymethyl halide, e.g. an acetoxymethyl halide to give an acyloxymethyl ester of a carboxyalkyl group R (esterification).

(viii) a nitrile group is hydrolysed or alcoholised to give an acid, amide or ester group R (hydrolysis or alcoholysis).

(ix) an acid group or its functional derivative is reacted with ammonia, or an ammonium salt is heated to give a carboxamidoalkyl group R (amidation).

(x) a nitrile group is reacted with hydrogen sulphide to give a thiocarboxamidoalkyl group R (thioamidation).

(xi) a hydroxymethyl radical is reacted with a halogenating agent to give a halomethyl radical which is subjected to step (i) or (ii), or the hydroxymethyl radical is oxidised to a formyl radical which is condensed with a malonic acid or malonic ester by a Knoevenagel reaction, thereby splitting off carbon dioxide to give an acrylic acid or ester group R (chain extension and splitting off carbon dioxide).

(xii) a group $—C_nH_{2n}—M$ where M is an alkali metal atom is reacted with a haloaliphatic acid ester to give a carboalkoxyalkyl group R which can be hydrolysed to a caboxyalkyl group R (chain extension and hydrolysis).

(xiii) a methyl group is halogenated, e.g. with N-bromosuccinimide and the halomethyl group is subjected to step (i) or (ii) or is oxidised to a formyl group by the Sommelet reaction and the formyl radical is condensed with a malonic acid or ester by a Knoevenagel reaction, thereby splitting off carbon dioxide to give an acrylic acid or ester group R (chain extension and splitting off carbon dioxide).

(xiv) reducing an acrylic-acid or ester group to a propionic acid or ester group R by catalytic hydrogenation (reduction).

(xv) A —CHO, —COOH or —COOAlkyl group is reduced with a hydride transfer agent such as a metal hydride to give the corresponding alcohol which may then be treated as in (xi) above.

(xvi) A halo group is reacted with magnesium to form the corresponding Grignard reagent and then treated with carbon dioxide to give the corresponding carboxylic acid group which may then be treated as in (ii) or (xv) above. (xvii) a hydroxyl group is halogenated with such reagents as phosphorus halides or oxyhalides or thionyl chloride and the halo group treated as in (xvi) above.

(xviii) a methyl group is oxidised to the corresponding carboxyl group which is treated as in (iii) or (xv) above.

(xix) a ketone group is reduced to the corresponding alcohol or treated with an alkyl magnesium halide to give the tertiary alcohol which may then be treated as in (xi) above.

(xx) a propiolic acid group is reduced to the corresponding ethylenically unsaturated acid by known methods.

As already indicated, the preferred compounds of the invention are those of formula II, and the preferred method of making these is essentially that of Section A (iii) in which a hydrazone of formula

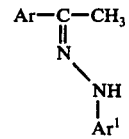

is reacted with the adduct formed from phosphoryl chloride and dimethylformamide followed by hydrolysis of the immonium perchlorate formed to give the pyrazole of formula

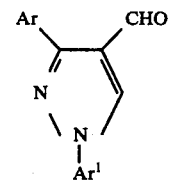

The aldehyde is then reduced to the corresponding alcohol, chlorinated with thionyl chloride to give the chloromethyl derivative which is reacted with sodium cyanide and the nitrile hydrolysed to the acetic acid or acetamide derivative.

The pyrazoles provided by the invention are capable of forming acid addition salts with pharmaceutically acceptable acids and the invention also provides such salts. Suitable acids include mineral acids such as hydrochloric, sulphuric, nitric, phosphoric and perchloric acid, and also organic acids such as oxalic, methanesulphonic and p-toluenesulphonic acid.

As the compounds of general formula (I) generally show pharmaceutical activity such as anti-inflammatory activity, the invention provides a pharmaceutical composition commprising a compound of general formula (I), and a pharmaceutically acceptable carrier.

When the compounds of this invention are employed as anti-inflammatory agents they can be administered to warmblooded animals, e.g. mice, rats, rabbits, dogs, cats, monkeys, etc., alone or as a pharmaceutical composition in combination with pharmaceutically acceptable carriers. The carrier may be solid, liquid or creamlike and any suitable carrier known to the art can be used. the composition can be in unit dose form, for example as tablets or capsules or it can be in the form of a solution. The compositions can be administered orally or parenterally by injection and the composition can, for parenteral administration, be in the form of a sterile solution or suspension containing other solutes, for example enough saline or glucose to render the solution isotonic. The particular carrier and proportion of carrier to active compound will be determined by the nature of the compound, and the chosen route of administration and standard pharmaceutical practice.

The dosage of the active compound will vary with the form of administration and the particular compound chosen. Furthermore, it will vary with the particular subject under treatment. Generally, treatment is initiated with small dosages substantially less than the optimum does of the compound. Thereafter, the dosage is increased by small increments until the optimum effect under the circumstances is reached. In general, the compounds of this invention are most desirably administered at a concentration level that will generally afford effective results without causing any harmful or deleterious side effects.

The following Examples illustrate the invention

EXAMPLE 1

1,3-Diphenylpyrazol-4-ylacetic acid (a) 1,3-Diphenylpyrazole-4-carboxaldehyde (16.0 g.) was dissolved in benzene (100 ml.) and a 70% benzene solution of sodium dihydrobis(2-methoxyethoxy)aluminate (14.0 ml.) was added dropwise at room temperature. The solution was heated under reflux for 2 hours and then water and an excess of 2N hydrochloric acid added at room temperature. The benzene layer was separated, washed with water, dried (MgSO$_4$) and evaporated to give a white solid which after recrystallisation from aqueous ethanol gave 10 g. of 1,3-diphenyl-4-hydroxymethylpyrazole, m.p. 98°–100° C. (Found: C, 76.8; H, 5.7; N, 11.2. C$_{16}$H$_{14}$N$_2$O requires C, 76.8; H, b 5.7; N, 11.2%).

(b) The hydroxymethyl compound (8.0 g.) of part (a) was dissolved in a mixture of pyridine (2.4 ml.) and methylene chloride (8.0 ml.). Thionyl chloride (1.1 g.) was added dropwise while maintaining the reaction temperature below 10° C., and after the addition reaction mixture was stirred at room temperature for 16 hours. The solution was poured into water and the resulting mixture extracted with methylene chloride. The organic extract was washed with saturated sodium hydrogen carbonate solution, water, 2N hydrochloric acid, water, dried (MgSO$_4$) and evaporated to give a white solid which after recrystallisation from a mixture of benzene and petroleum ether (b.p. 60°–80° C) gave 7.4 g. of 4-chloromethyl-1,3-diphenylpyrazole, m.p. 82°–83° C (Found: C, 71.3; H, 5.0; N, 10.5. C$_{16}$H$_{13}$ClN$_2$ requires C, 71.5; H, 4.9; N, 10.4%).

(c) The chloromethyl compound (2.0 g.) of part (b) was dissolved in dry dimethylsulphoxide (10 ml.) and heated to 40° C when sodium cyanide (0.9 g.) was added. The reaction mixture was stirred and maintained at 40° C for 2 hours and then poured into an excess of water. The precipitated solid was filtered off and recrystallised from a mixture of benzene and petroleum ether (b.p. 40°–60° C) to give 1.5 g. of 4-cyanomethyl-1,3-diphenyl-pyrazole, m.p. 87°–88° C. (Found: C, 78.8; H, 5.1; N, 16.3. C$_{17}$H$_{13}$N$_3$ requires C, 78.7; H, 5.05; N, 16.2%).

(d) A solution of the cyanomethyl compound (2.0 g.) of part (c) in a mixture of ethanol(14.0 ml.) and water (6.0 ml.) containing sodium hydroxide (2.0 g.) was heated under reflux for 2 hours. The solvent was then evaporated, the residue dissolved in water, washed with ether and then acidified with concentrated hydrochloric acid. The mixture was extracted with ether and the organic extract washed with water, dried (MgSO$_4$) and evaporated to give a white solid which was recrystallised from a mixture of benzene and petroleum ether (b.p. 40°–60° C) to give 1.5 g. of the title acid, m.p. 120°–121° C. (Found: C, 73.5; H, 5.0; N, 10.1. C$_{17}$H$_{14}$N$_2$O$_2$ requires C, 73.4; H, 5.1; N, 10.1%).

EXAMPLE 2

3-(p-Chlorophenyl)-1-phenylpyrazol-4-ylacetic acid (a) 3-(p-Chlorophenyl)-1-phenylpyrazole-4-carboxaldehyde (13.6 g.) was reduced as described in Example 1(a) to give 9.2 g. of 3-(p-chlorophenyl)-4-hydroxymethyl-1-phenylpyrazole, m.p. 138°–140° C. (Found: C, 67.8; H, 4.6; N, 10.0. C$_{16}$H$_{13}$ClN$_2$O requires C, 67.5; H, 4.6; N, 9.8%).

(b) The hydroxymethyl compound (9.0 g.) of part (a) was chlorinated as in Example 1(b) to give 6.4 g. of 4-chloromethyl-3-(p-chlorophenyl)-1-phenylpyrazole, m.p. 105°–106° C. (Found: C, 63.1; H, 4.1; N, 9.45. C$_{16}$H$_{12}$Cl$_2$N$_2$ requires C, 63.4; H, 4.0; N, 9.25%).

(c) The chloromethyl compound (5.0 g.) of part (b) was treated with sodium cyanide as described in Example 1(c) to give 3.8 g. of 3-(p-chlorophenyl)-4-cyanomethyl-1-phenylpyrazole.

(d) The cyanomethyl compound (3.8 g.) of part (c) was hydrolysed by the method of Example 1(d) to give 2.54 g. of the title acid, m.p. 147°–148° C. (Found: C, 65.5; H, 4.2; N, 8.85. C$_{17}$H$_{13}$ClN$_2$O$_3$ requires C, 65.3; H, 4.2; N, 9.0%).

EXAMPLE 3

3-(p-Chlorophenyl)-1-(m-methylphenyl)-pyrazol-4-ylacetamide (a)
3-(p-Chlorophenyl)-1-(m-methylphenyl)pyrazole-4-carboxaldehyde (14.8 g.) was reduced as described in Example 1(a) to give 11.5 g. of 3-(p-chlorophenyl)-4-hydroxymethyl-1-(m-methylphenyl)pyrazole, m.p. 113°–114° C. (Found C, 68.65; H, 5.1; N, 9.5. C$_{17}$H$_{15}$ClN$_2$O requires C, 68.4; H, 5.1; N, 9.7%).

(b) The hydroxymethyl compound (10.0 g.) of part (a) was chlorinated as in Example 1(b) to give 8.8 g. of 4-chloromethyl-3-(p-chlorophenyl)-1-(m-methylphenyl)pyrazole, m.p. 83°–84° C. (Found: C, 64.4; H, 4.5; N, 8.8. C$_{17}$H$_{14}$Cl$_2$N$_2$ requires C, 64.4; H, 4.45; N, 8.8%).

(c) The chloromethyl compound (9.97 g.) of part (b) was treated with sodium cyanide as described in Example 1(c) to give 4.93 g. of 3-(p-chlorophenyl)-4-cyanomethyl-1-(m-methylphenyl)pyrazole, m.p. 114°–115° C. (Found C, 70.5; H, 4.6; N, 13.8. $C_{18}H_{14}ClN_3$ requires C, 70.3; H, 4.6; N, 13.7%).

(d) A solution of the cyanomethyl compound (7.6 g.) of part (c) in a mixture of ethanol (90 ml.) and water (40 ml.) containing sodium hydroxide (1.0 g.) was heated under reflux for 3 hours. The solvent was evaporated and the residue treated with water and ether to give a solid residue which after recrystallisation from aqueous ethanol gave 3.4 g, of the title amide, m.p. 190°–192° C. (Found: C, 66.2; H, 5.0; N, 12.8. $C_{18}H_{16}ClN_3O$ requires C, 66.4; H, 4.95; N, 12.9%).

EXAMPLE 4

3-(p-Chlorophenyl)-1-(m-methylphenyl)-pyrazole-4-ylacetic acid

A solution of the acetamide (5.3 g.) of part (d) of Example 3 in a mixture of ethanol (49 ml.) and water (21 g.) containing sodium hydroxide (5.3 g.) was heated under reflux for 4 hours. The solvent was evaporated and the residue dissolved in water, washed with ether and then acidified with concentrated hydrochloric acid. The mixture was extracted with ether and the organic extract washed with water, dried ($MgSO_4$) and evaporated to give a gum which was crystallised from a mixture of benzene and petroleum ether (b.p. 40°–60° C) to give 3.5 g. of the title acid, m.p. 129°–130° C. (Found C, 66.4; H, 4.8; N, 8.6. $C_{18}H_{15}ClN_2O_2$ requires C, 66.2; H, 4.6; N, 8.6%).

EXAMPLE 5

β-[3-(p-Chlorophenyl)-1-phenylpyrazol-4-yl]acrylic acid 3-(p-Chlorophenyl)-1-phenylpyrazol-4-ylcarboxaldehyde (5.6 g.), malonic acid (2.08 g.) and pyridine (2.5 ml.) were boiled together under reflux in absolute ethanol (25 ml) for 2 hours. The crystalline product, which formed on cooling, was filtered and dissolved in dimethylformamide (50 ml.). The solution was boiled under reflux for 4 hours and then poured into water (500 ml.). The precipitated solid was collected and recrystallised from glacial acetic acid to give white crystals of the title compound (2.5 g.), m.p. 227°–228° C. (Found; C, 67.7; H, 4.1; N, 9.1. $C_{18}H_{13}ClN_2O_2$ requires C, 67.8; H, 4.0; N, 8.7%).

EXAMPLE 6

Following the procedure of Example 1, the following carboxaldehydes gave the products indicated:

| Carboxaldehyde. | Product. |
| --- | --- |
| 1-Phenyl-3-(p-fluorophenyl)-pyrazole-4-carboxaldehyde. | 1-Phenyl-3-(p-fluorophenyl)-pyrazol-4-ylacetic acid. |
| 1-Phenyl-3-(p-bromophenyl)-pyrazole-4-carboxaldehyde. | 1-Phenyl-3-(p-bromophenyl)-pyrazol-4-ylacetic acid. |
| 1-Phenyl-3-(o-chlorophenyl)-pyrazole-4-carboxaldehyde. | 1-Phenyl-3-(o-chlorophenyl)-pyrazol-4-ylacetic acid. |
| 1-Phenyl-3-(o-methylphenyl)-pyrazole-4-carboxaldehyde. | 1-Phenyl-3-(o-methylphenyl)-pyrazol-4-ylacetic acid. |
| 1-Phenyl-3-(m-methylphenyl)-pyrazole-4-carboxaldehyde. | 1-Phenyl-3-(m-methylphenyl)-pyrazol-4-ylacetic acid. |
| 1-Phenyl-3-(p-methylphenyl)-pyrazole-4-carboxaldehyde. | 1-Phenyl-3-(p-methylphenyl)-pyrazol-4-ylacetic acid. |
| 1-Phenyl-3-(p-butylphenyl)-pyrazole-4-carboxaldehyde. | 1-Phenyl-3-(p-butylphenyl)-pyrazol-4-ylacetic acid. |
| 1-Phenyl-3-(p-methoxyphenyl)-pyrazole-4-carboxaldehyde. | 1-Phenyl-3-(p-methoxyphenyl)-pyrazol-4-ylacetic acid. |
| 1-Phenyl-3-(p-butoxyphenyl)-pyrazole-4-carboxaldehyde. | 1-Phenyl-3-(p-butoxyphenyl)-pyrazol-4-ylacetic acid. |
| 1-Phenyl-3-(3,4-dimethoxyphenyl)pyrazole-4-carboxaldehyde. | 1-Phenyl-3-(3,4-dimethoxyphenyl)pyrazol-4-ylacetic acid. |
| 1-Phenyl-3-(p-hydroxyphenyl)-pyrazole-4-carboxaldehyde. | 1-Phenyl-3-(p-hydroxyphenyl)-pyrazol-4-ylacetic acid. |
| 1-Phenyl-3-(p-nitrophenyl)-pyrazole-4-carboxaldehyde. | 1-Phenyl-3-(p-nitrophenyl)-pyrazol-4-ylacetic acid. |
| 1-Phenyl-3-(p-dimethylaminophenyl)pyrazole-4-carboxaldehyde. | 1-Phenyl-3-(p-dimethylaminophenyl)pyrazol-4-ylacetic acid. |
| 1-Phenyl-3-(p-dimethylaminophenyl)pyrazole-4-carboxaldehyde. | 1-Phenyl-3-(p-dimethylaminophenyl)pyrazol-4-ylacetic acid hydrochloride. |
| 1-Phenyl-3-(m-trifluoromethylphenyl)pyrazole-4-carboxaldehyde. | 1-Phenyl-3-(m-trifluoromethylphenyl)pyrazol-4-ylacetic acid. |
| 1-Phenyl-3-(p-methylthiophenyl)pyrazole-4-carboxaldehyde. | 1-Phenyl-3-(p-methylthiophenyl)pyrazol-4-ylacetic acid. |
| 1-Phenyl-3-(naphth-1-yl)-pyrazole-4-carboxaldehyde. | 1-Phenyl-3-(naphth-1-yl)-pyrazol-4-ylacetic acid. |
| 1-Phenyl-3-(naphth-2-yl)-pyrazole-4-carboxaldehyde. | 1-Phenyl-3-(naphth-2-yl)-pyrazol-4-ylacetic acid. |
| 1-Phenyl-3-(fur-2-yl)-pyrazole-4-carboxaldehyde. | 1-Phenyl-3-(fur-2-yl)-pyrazol-4-ylacetic acid. |
| 1-Phenyl-3-(fur-3-yl)-pyrazole-4-carboxaldehyde. | 1-Phenyl-3-(fur-3-yl)-pyrazol-4-ylacetic acid. |
| 1-Phenyl-3-(thien-2-yl)-pyrazole-4-carboxaldehyde. | 1-Phenyl-3-(thien-2-yl)-pyrazol-4-ylacetic acid. |
| 1-Phenyl-3-(thien-3-yl)-pyrazole-4-carboxaldehyde. | 1-Phenyl-3-(thien-3-yl)-pyrazol-4-ylacetic acid. |
| 1-Phenyl-3-(pyrid-2-yl)-pyrazole-4-carboxaldehyde. | 1-Phenyl-3-(pyrid-2-yl)-pyrazol-4-ylacetic acid. |
| 1-Phenyl-3-(pyrid-3-yl)-pyrazole-4-carboxaldehyde. | 1-Phenyl-3-(pyrid-3-yl)-pyrazol-4-ylacetic acid. |
| 1-Phenyl-3-(pyrid-4-yl)-pyrazole-4-carboxaldehyde. | 1-Phenyl-3-(pyrid-4-yl)-pyrazol-4-ylacetic acid. |
| 1-Phenyl-3-(indol-2-yl)-pyrazole-4-carboxaldehyde. | 1-Phenyl-3-(indol-2-yl)-pyrazol-4-ylacetic acid. |
| 1-Phenyl-3-(indol-3-yl)-pyrazole-4-carboxaldehyde. | 1-Phenyl-3-(indol-3-yl)-pyrazol-4-ylacetic acid. |
| 1-Phenyl-3-(pyrrol-2-yl)-pyrazole-4-carboxaldehyde. | 1-Phenyl-3-(pyrrol-2-yl)-pyrazol-4-ylacetic acid. |
| 1-Phenyl-3-(pyrrol-3-yl)-pyrazole-4-carboxaldehyde. | 1-Phenyl-3-(pyrrol-3-yl)-pyrazol-4-ylacetic acid. |

EXAMPLE 7

Following the procedure of Example 1, the following carboxaldehydes gave the products indicated:

| Carboxaldehyde. | Product. |
| --- | --- |
| 3-Phenyl-1-(p-fluorophenyl)-pyrazole-4-carboxaldehyde. | 3-Phenyl-1-(p-fluorophenyl)-pyrazol-4-ylacetic acid. |
| 3-Phenyl-1-(p-bromophenyl)-pyrazole-4-carboxaldehyde. | 3-Phenyl-1-(p-bromophenyl)-pyrazol-4-ylacetic acid. |
| 3-Phenyl-1-(o-chlorophenyl)-pyrazole-4-carboxaldehyde. | 3-Phenyl-1-(o-chlorophenyl)-pyrazol-4-ylacetic acid. |
| 3-Phenyl-1-(o-methylphenyl)-pyrazole-4-carboxaldehyde. | 3-Phenyl-1-(o-methylphenyl)-pyrazol-4-ylacetic acid. |
| 3-Phenyl-1-(m-methylphenyl)-pyrazole-4-carboxaldehyde. | 3-Phenyl-1-(m-methylphenyl)-pyrazol-4-ylacetic acid. |
| 3-Phenyl-1-(p-methylphenyl)-pyrazole-4-carboxaldehyde. | 3-Phenyl-1-(p-methylphenyl)-pyrazol-4-ylacetic acid. |
| 3-Phenyl-1-(p-butylphenyl)-pyrazole-4-carboxaldehyde. | 3-Phenyl-1-(p-butylphenyl)-pyrazol-4-ylacetic acid. |
| 3-Phenyl-1-(p-methoxyphenyl)-pyrazole-4-carboxaldehyde. | 3-Phenyl-1-(p-methoxyphenyl)-pyrazol-4-ylacetic acid. |
| 3-Phenyl-1-(p-butoxyphenyl)-pyrazole-4-carboxaldehyde. | 3-Phenyl-1-(p-butoxyphenyl)-pyrazol-4-ylacetic acid. |
| 3-Phenyl-1-(3,4-dimethoxyphenyl)pyrazole-4-carboxaldehyde. | 3-Phenyl-1-(3,4-dimethoxyphenyl)pyrazol-4-ylacetic acid. |
| 3-Phenyl-1-(p-hydroxyphenyl)-pyrazole-4-carboxaldehyde. | 3-Phenyl-1-(p-hydroxyphenyl)-pyrazol-4-ylacetic acid. |
| 3-Phenyl-1-(p-nitrophenyl)-pyrazole-4-carboxaldehyde. | 3-Phenyl-1-(p-nitrophenyl)-pyrazol-4-ylacetic acid. |
| 3-Phenyl-1-(p-dimethylaminophenyl)pyrazole-4-carboxaldehyde. | 3-Phenyl-1-(p-dimethylaminophenyl)pyrazol-4-ylacetic acid. |
| 3-Phenyl-1-(m-trifluoromethylphenyl)pyrazole-4-carboxaldehyde. | 3-Phenyl-1-(m-trifluoromethylphenyl)pyrazol-4-ylacetic acid. |
| 3-Phenyl-1-(p-methylthiophenyl)pyrazole-4-carboxaldehyde. | 3-Phenyl-1-(p-methylthiophenyl)pyrazol-4-ylacetic acid. |
| 3-Phenyl-1-(naphth-1-yl)- | 3-Phenyl-1-(naphth-1-yl)- |

-continued

| Carboxaldehyde. | Product. |
|---|---|
| pyrazole-4-carboxaldehyde. | pyrazol-4-ylacetic acid. |
| 3-Phenyl-1-(naphth-2-yl)-pyrazole-4-carboxaldehyde. | 3-Phenyl-1-(naphth-2-yl)-pyrazol-4-ylacetic acid. |
| 3-Phenyl-1-(fur-2-yl)-pyrazole-4-carboxaldehyde. | 3-Phenyl-1-(fur-2-yl)-pyrazol-4-ylacetic acid. |
| 3-Phenyl-1-(fur-3-yl)-pyrazole-4-carboxaldehyde. | 3-Phenyl-1-(fur-3-yl)-pyrazol-4-ylacetic acid. |
| 3-Phenyl-1-(thien-2-yl)-pyrazole-4-carboxaldehyde. | 3-Phenyl-1-(thien-2-yl)-pyrazol-4-ylacetic acid. |
| 3-Phenyl-1-(thien-3-yl)-pyrazole-4-carboxaldehyde. | 3-Phenyl-1-(thien-3-yl)-pyrazol-4-ylacetic acid. |
| 3-Phenyl-1-(pyrid-2-yl)-pyrazole-4-carboxaldehyde. | 3-Phenyl-1-(pyrid-2-yl)-pyrazol-4-ylacetic acid. |
| 3-Phenyl-1-(pyrid-3-yl)-pyrazole-4-carboxaldehyde. | 3-Phenyl-1-(pyrid-3-yl)-pyrazol-4-ylacetic acid. |
| 3-Phenyl-1-(pyrid-4-yl)-pyrazole-4-carboxaldehyde. | 3-Phenyl-1-(pyrid-4-yl)-pyrazol-4-ylacetic acid. |
| 3-Phenyl-1-(indol-2-yl)-pyrazole-4-carboxaldehyde. | 3-Phenyl-1-(indol-2-yl)-pyrazol-4-ylacetic acid. |
| 3-Phenyl-1-(indol-3-yl)-pyrazole-4-carboxaldehyde. | 3-Phenyl-1-(indol-3-yl)-pyrazole-4-ylacetic acid. |
| 3-Phenyl-1-(pyrrol-2-yl)-pyrazole-4-carboxaldehyde. | 3-Phenyl-1-(pyrrol-2-yl)-pyrazol-4-ylacetic acid. |
| 3-Phenyl-1-(pyrrol-3-yl)-pyrazole-4-carboxaldehyde. | 3-Phenyl-1-(pyrrol-3-yl)-pyrazol-4-ylacetic acid. |
| 3-Phenyl-1-(p-dimethylaminophenyl)pyrazole-4-carboxaldehyde. | 3-Phenyl-1-(p-dimethylaminophenyl)pyrazol-4-ylacetic acid methiodide. |

EXAMPLE 8

Following the procedure of Example 1, the following carboxaldehydes gave the products indicated:

| Carboxaldehyde | Product. |
|---|---|
| 1,3-Di-(p-chlorophenyl)-pyrazole-4-carboxaldehyde | 1,3-Di-(p-chlorophenyl)-pyrazol-4-ylacetic acid. |
| 1-(p-Methylphenyl)-3-(p-chlorophenyl)pyrazole-4-carboxaldehyde. | 1-(p-Methylphenyl)-3-(p-chlorophenyl)pyrazol-4-ylacetic acid. |
| 1,3-Di-(p-methylphenyl)-pyrazole-4-carboxaldehyde. | 1,3-Di-(p-methylphenyl)-pyrazol-4-ylacetic acid. |
| 1,3-Di-(p-fluorophenyl)-pyrazole-4-carboxaldehyde. | 1,3-Di-(p-fluorophenyl)-pyrazol-4-ylacetic acid. |
| 1,3-Di-(p-bromophenyl)-pyrazole-4-carboxaldehyde. | 1,3-Di-(p-bromophenyl)-pyrazol-4-ylacetic acid. |
| 1,3-Di-(o-chlorophenyl)-pyrazole-4-carboxaldehyde. | 1,3-Di-(o-chlorophenyl)-pyrazol-4-ylacetic acid. |
| 1,3-Di-(o-methylphenyl)-pyrazole-4-carboxaldehyde. | 1,3-Di-(o-methylphenyl)-pyrazol-4-ylacetic acid. |
| 1,3-Di-(m-methylphenyl-pyrazole-4-carboxaldehyde. | 1,3-Di-(m-methylphenyl)-pyrazol-4-ylacetic acid. |
| 1,3-Di-(p-butylphenyl)-pyrazole-4-carboxaldehyde. | 1,3-Di-(p-butylphenyl)-pyrazol-4-ylacetic acid. |
| 1,3-Di-(p-methoxyphenyl)-pyrazole-4-carboxaldehyde. | 1,3-Di-(p-methoxyphenyl)-pyrazol-4-ylacetic acid. |
| 1,3-Di-(p-dimethylaminophenyl)pyrazole-4-carboxaldehyde. | 1,3-Di-(p-dimethylaminophenyl)pyrazol-4-ylacetic acid. |
| 1,3-Di-(m-trifluoromethylphenyl)pyrazole-4-carboxaldehyde. | 1,3-Di-(m-trifluoromethylphenyl)pyrazol-4-ylacetic acid. |

EXAMPLE 9

Following the procedure of Example 5, the following carboxaldehydes gave the products indicated:

| Carboxaldehyde. | Product. |
|---|---|
| 1-Phenyl-3-(p-fluorophenyl)-pyrazole-4-carboxaldehyde. | β-[-Phenyl-3-(p-fluorophenyl)pyrazol-4-yl]-acrylic acid. |
| 1-Phenyl-3-(p-bromophenyl)-pyrazole-4-carboxaldehyde. | β-[1-Phenyl-3-(p-bromophenyl)pyrazol-4-yl]-acrylic acid. |
| 1-Phenyl-3-(o-chlorophenyl)-pyrazole-4-carboxaldehyde. | β-[1-phenyl-3-(o-chlorophenyl)pyrazol-4-yl]-acrylic acid. |
| 1-Phenyl-3-(o-methylphenyl)-pyrazole-4-carboxaldehyde. | β-[1-Phenyl-3-(o-methylphenyl)pyrazol-4-yl]-acrylic acid. |
| 1-Phenyl-3-(m-methylphenyl)-pyrazole-4-carboxaldehyde. | β-[1-Phenyl-3-(m-methylphenyl)pyrazol-4-yl]-acrylic acid. |
| 1-Phenyl-3-(p-methylphenyl)-pyrazole-4-carboxaldehyde. | β-[1-Phenyl-3-(p-methylphenyl)pyrazol-4-yl]-acrylic acid. |
| 1-Phenyl-3-(p-butylphenyl)-pyrazole-4-carboxaldehyde. | β-[1-Phenyl-3-(p-butylphenyl)pyrazol-4-yl]-acrylic acid. |
| 1-Phenyl-3-(p-methoxyphenyl)-pyrazole-4-carboxaldehyde. | β-[1-Phenyl-3-(p-methoxyphenyl)pyrazol-4-yl]-acrylic acid. |
| 1-Phenyl-3-(p-butoxyphenyl)-pyrazole-4-carboxaldehyde. | β-[1-Phenyl-3-(p-butoxyphenyl)pyrazol-4-yl]-acrylic acid. |
| 1-Phenyl-3-(3,4-dimethoxyphenyl)pyrazole-4-carboxaldehyde. | β-[1-Phenyl-3-(3,4-dimethoxyphenyl)pyrazol-4-yl]-acrylic acid. |
| 1-Phenyl-3-(p-hydroxyphenyl)-pyrazole-4-carboxaldehyde. | β-[1-Phenyl-3-(p-hydroxyphenyl)pyrazol-4-yl]-acrylic acid. |
| 1-Phenyl-3-(p-nitrophenyl)-pyrazole-4-carboxaldehyde. | β-[1-Phenyl-3-(p-nitrophenyl)pyrazol-4-yl]-acrylic acid. |
| 1-Phenyl-3-(p-dimethylaminophenyl)pyrazole-4-carboxaldehyde. | β-[1-Phenyl-3-(p-dimethylaminophenyl)pyrazol-4-yl]-acrylic acid. |
| 1-Phenyl-3-(m-trifluoromethylphenyl)pyrazole-4-carboxaldehyde. | β-[1-Phenyl-3-(m-trifluoromethylphenyl)pyrazol-4-yl]-acrylic acid. |
| 1-Phenyl-3-(p-methylthiophenyl)pyrazole-4-carboxaldehyde. | β-[1-Phenyl-3-(p-methylthiophenyl)pyrazol-4-yl]-acrylic acid. |
| 1-Phenyl-3-(naphth-1-yl)-pyrazole-4-carboxaldehyde. | β-[1-Phenyl-3-(napth-1-yl)-pyrazol-4-yl]acrylic acid. |
| 1-Phenyl-3-(naphth-2-yl)-pyrazole-4-carboxaldehyde. | β-[1-Phenyl-3-(naphth-2-yl)-pyrazol-4-yl]acrylic acid. |
| 1-Phenyl-3-(fur-2-yl)-pyrazole-4-carboxaldehyde. | β-[1-Phenyl-3-(fur-2-yl)-pyrazol-4-yl]acrylic acid. |
| 1-Phenyl-3-(fur-3-yl)-pyrazole-4-carboxaldehyde. | β-[1-Phenyl-3-(fur-3-yl)-pyrazol-4-yl]acrylic acid. |
| 1-Phenyl-3-(thien-2-yl)-pyrazole-4-carboxaldehyde. | β-[1-Phenyl-3-(thien-2-yl)-pyrazol-4-yl]acrylic acid. |
| 1-Phenyl-3-(thien-3-yl)-pyrazole-4-carboxaldehyde. | β-[1-Phenyl-3-(thien-3-yl)-pyrazol-4-yl]acrylic acid. |
| 1-Phenyl-3-(pyrid-2-yl)-pyrazole-4-carboxaldehyde. | β-[1-Phenyl-3-(pyrid-2-yl)-pyrazol-4-yl]acrylic acid. |
| 1-Phenyl-3-(pyrid-3-yl)-pyrazole-4-carboxaldehyde. | β-[1-Phenyl-3-(pyrid-3-yl)-pyrazol-4-yl]acrylic acid. |
| 1-Phenyl-3-(pyrid-4-yl)-pyrazole-4-carboxaldehyde. | β-[1-Phenyl-3-(pyrid-4-yl)-pyrazol-4-yl]acrylic acid. |
| 1-Phenyl-3-(indol-2-yl)-pyrazole-4-carboxaldehyde. | β-[1-Phenyl-3-(indol-2-yl)-pyrazol-4-yl]acrylic acid. |
| 1-Phenyl-3-(indol-3-yl)-pyrazole-4-carboxaldehyde. | β-[1-Phenyl-3-(indol-3-yl)-pyrazol-4-yl]acrylic acid. |
| 1-Phenyl-3-(pyrrol-2-yl)-pyrazole-4-carboxaldehyde. | β-[1-Phenyl-3-(pyrrol-2-yl)-pyrazol-4-yl]acrylic acid. |
| 1-Phenyl-3-(pyrrol-3-yl)-pyrazole-4-carboxaldehyde. | β-[1-Phenyl-3-(pyrrol-3-yl)-pyrazol-4-yl]acrylic acid. |

EXAMPLE 10

Following the procedure of Example 5, the following carboxaldehydes gave the products indicated:

| Carboxaldehyde. | Product. |
|---|---|
| 3-Phenyl-1-(p-fluorophenyl)-pyrazole-4-carboxaldehyde. | β-[3-Phenyl-1-(p-fluorophenyl)pyrazol-4-yl]-acrylic acid. |
| 3-Phenyl-1-(p-bromophenyl)-pyrazole-4-carboxaldehyde. | β-[3-Phenyl-1-(p-bromophenyl)pyrazol-4-yl]-acrylic acid. |
| 3-Phenyl-1-(o-chlorophenyl)-pyrazole-4-carboxaldehyde. | β-[3-phenyl-1-(o-chlorophenyl)pyrazol-4-yl]-acrylic acid. |
| 3-Phenyl-1-(o-methylphenyl)-pyrazole-4-carboxaldehyde. | β-[3-Phenyl-1-(o-methylphenyl)pyrazol-4-yl]-acrylic acid. |
| 3-Phenyl-1-(m-methyphenyl)-pyrazole-4-carboxaldehyde. | β-[3-Phenyl-1-(m-methylphenyl)pyrazol-4-yl]-acrylic acid. |
| 3-Phenyl-1-(p-methylphenyl)-pyrazole-4-carboxaldehyde. | β-[3-Phenyl-1-(p-methylphenyl)pyrazol-4-yl]-acrylic acid. |
| 3-Phenyl-1-(p-butylphenyl)-pyrazole-4-carboxaldehyde. | β-[3-Phenyl-1-(p-butylphenyl)pyrazol-4-yl]-acrylic acid. |
| 3-Phenyl-1-(p-methoxyphenyl)-pyrazole-4-carboxaldehyde. | β-[3-Phenyl-1-(p-methoxyphenyl)pyrazol-4-yl]-acrylic acid. |

-continued

| Carboxaldehyde. | Product. |
| --- | --- |
| 3-Phenyl-1-(p-butoxyphenyl)-pyrazole-4-carboxaldehyde. | β-[3-Phenyl-1-(p-butoxyphenyl)pyrazol-4-yl]acrylic acid. |
| 3-Phenyl-1-(3,4-dimethoxyphenyl)pyrazole-4-carboxaldehyde. | β-[3-Phenyl-1-(3,4-dimethoxyphenyl)pyrazol-4-yl]acrylic acid. |
| 3-Phenyl-1-(p-hydroxyphenyl)-pyrazole-4-carboxaldehyde. | β-[3-Phenyl-1-(p-hydroxyphenyl)pyrazol-4-yl]acrylic acid. |
| 3-Phenyl-1-(p-nitrophenyl)-pyrazole-4-carboxaldehyde. | β-[3-Phenyl-1-(p-nitrophenyl)pyrazol-4-yl]acrylic acid. |
| 3-Phenyl-1-(p-dimethylaminophenyl)pyrazole-4-carboxaldehyde. | β-[3-Phenyl-1-(p-dimethylaminophenyl)pyrazol-4-yl]acrylic acid. |
| 3-Phenyl-1-(m-trifluoromethylphenyl)pyrazole-4-carboxaldehyde. | β-[3-Phenyl-1-(m-trifluoromethylphenyl)pyrazol-4-yl]acrylic acid. |
| 3-Phenyl-1-(p-methylthiophenyl)pyrazole-4-carboxaldehyde. | β-[3-Phenyl-1-(p-methylthiophenyl)pyrazol-4-yl]acrylic acid. |
| 3-Phenyl-1-(naphth-1-yl)-pyrazole-4-carboxaldehyde. | β-[3-Phenyl-1-(naphth-1-yl)-pyrazol-4-yl]acrylic acid. |
| 3-Phenyl-1-(naphth-2-yl)-pyrazole-4-carboxaldehyde. | β-[3-Phenyl-1-(naphth-2-yl)-pyrazol-4-yl]acrylic acid. |
| 3-Phenyl-1-(fur-2-yl)-pyrazole-4-carboxaldehyde. | β-[3-Phenyl-1-(fur-2-yl)-pyrazol-4-yl]acrylic acid. |
| 3-Phenyl-1-(fur-3-yl)-pyrazole-4-carboxaldehyde. | β-[3-Phenyl-1-(fur-3-yl)-pyrazol-4-yl]acrylic acid. |
| 3-Phenyl-1-(thien-2-yl)-pyrazole-4-carboxaldehyde. | β-[3-Phenyl-1-(thien-2-yl)-pyrazol-4-yl]acrylic acid. |
| 3-Phenyl-1-(thien-3-yl)-pyrazole-4-carboxaldehyde. | β-[3-Phenyl-1-(thien-3-yl)-pyrazol-4-yl]acrylic acid. |
| 3-Phenyl-1-(pyrid-2-yl)-pyrazole-4-carboxaldehyde. | β-[3-Phenyl-1-(pyrid-2-yl)-pyrazol-4-yl]acrylic acid. |
| 3-Phenyl-1-(pyrid-3-yl)-pyrazole-4-carboxaldehyde. | β-[3-Phenyl-1-(pyrid-3-yl)-pyrazol-4-yl]acrylic acid. |
| 3-Phenyl-1-(pyrid-4-yl)-pyrazole-4-carboxaldehyde. | β-[3-Phenyl-1-(pyrid-4-yl)-pyrazol-4-yl]acrylic acid. |
| 3-Phenyl-1-(indol-2-yl)-pyrazole-4-carboxaldehyde. | β-[3-Phenyl-1-(indol-2-yl)-pyrazol-4-yl]acrylic acid. |
| 3-Phenyl-1-(indol-3-yl)-pyrazole-4-carboxaldehyde. | β-[3-Phenyl-1-(indol-3-yl)-pyrazol-4-yl]acrylic acid. |
| 3-Phenyl-1-(pyrrol-2-yl)-pyrazole-4-carboxaldehyde. | β-[3-Phenyl-1-(pyrrol-2-yl)-pyrazol-4-yl]acrylic acid. |
| 3-Phenyl-1-(pyrrol-3-yl)-pyrazole-4-carboxaldehyde. | β-[3-Phenyl-1-(pyrrol-3-yl)-pyrazole-4-yl]acrylic acid. |

EXAMPLE 11

Following the procedure of Example 5, the following carboxaldehydes gave the products indicated:

| Carboxaldehydes. | Product. |
| --- | --- |
| 1,3-Di-(p-chlorophenyl)-pyrazole-4-carboxaldehyde. | β-[1,3-Di-(p-chlorophenyl)-pyrazol-4-yl]acrylic acid. |
| 1-(p-Methylphenyl)-3-(p-chlorophenyl)pyrazole-4-carboxaldehyde. | β-[1-(p-Methylphenyl)-3-(p-chlorophenyl)pyrazol-4-yl]acrylic acid. |
| 1,3-Di-(p-methylphenyl)-pyrazole-4-carboxaldehyde. | β-[1,3-Di-(p-methylphenyl)-pyrazol-4-yl]acrylic acid. |
| 1,3-Di-(p-fluorophenyl)-pyrazole-4-carboxaldehyde. | β-[1,3-Di-(p-fluorophenyl)-pyrazol-4-yl]acrylic acid. |
| 1,3-Di-(p-bromophenyl)-pyrazole-4-carboxaldehyde. | β-[1,3-Di-(p-bromophenyl)-pyrazol-4-yl]acrylic acid. |
| 1,3-Di-(o-chlorophenyl)-pyrazole-4-carboxaldehyde. | β-[1,3-Di-(o-chlorophenyl)-pyrazol-4-yl]acrylic acid. |
| 1,3-Di-(o-methylphenyl)-pyrazole-4-carboxaldehyde. | β-[1,3-Di-(o-methylphenyl)-pyrazol-4-yl]acrylic acid. |
| 1,3-Di-(m-methylphenyl)-pyrazole-4-carboxaldehyde. | β-[1,3-Di-(m-methylphenyl)-pyrazol-4-yl]acrylic acid. |
| 1,3-Di-(p-butylphenyl)-pyrazole-4-carboxaldehyde. | β-[1,3-Di-(p-butylphenyl)-pyrazol-4-yl]acrylic acid. |
| 1,3-Di-(p-methoxyphenyl)-pyrazole-4-carboxaldehyde. | β-[1,3-Di-(p-methoxyphenyl)-pyrazol-4-yl]acrylic acid. |
| 1,3-Di-(p-dimethylaminophenyl)pyrazole-4-carboxaldehyde. | β-[1,3-Di-(p-dimethylaminophenyl)pyrazol-4-yl]acrylic acid. |
| 1,3-Di-(m-trifluoromethylphenyl)pyrazole-4-carboxaldehyde. | β-[1,3-Di-(m-trifluoromethylphenyl)pyrazol-4-yl]acrylic acid. |

EXAMPLE 12

β-[3-(p-Chlorophenyl)-1-phenylpyrazol-4-yl]propionic acid.

A mixture of the corresponding acrylic acid derivative of Example 5 (1.0 g.) and palladium-on-charcoal (0.25 g. of 10%) in ethanol (50 ml.) was shaken in an atmosphere of hydrogen until uptake of hydrogen had ceased. Removal of the catalyst by filtration, evaporation of the filtrate and recrystallisation of the residue gave 0.25 g. of the title compound.

EXAMPLE 13

Following the procedure of Example 12, the following acrylic acid derivatives were reduced to the propionic acids indicated:

| Acrylic Acid. | Propionic Acid. |
| --- | --- |
| β-[1-Phenyl-3-(p-fluorophenyl)pyrazol-4-yl]acrylic acid. | β-[1-Phenyl-3-(p-fluorophenyl)pyrazol-4-yl]propionic acid. |
| β-[1-Phenyl-3-(p-bromophenyl)pyrazol-4-yl]acrylic acid. | β-[1-Phenyl-3-(p-bromophenyl)pyrazol-4-yl]propionic acid. |
| β-[1-phenyl-3-(o-chlorophenyl)pyrazol-4-yl]acrylic acid. | β-[1-Phenyl-3-(o-chlorophenyl)pyrazol-4-yl]propionic acid. |
| β-[1-Phenyl-3-(o-methylphenyl)pyrazol-4-yl]acrylic acid. | β-[1-Phenyl-3-(o-methylphenyl)pyrazol-4-yl]propionic acid. |
| β-[1-Phenyl-3-(m-methylphenyl)pyrazol-4-yl]acrylic acid. | β-[1-Phenyl-3-(m-methylphenyl)pyrazol-4-yl]propionic acid. |
| β-[1-Phenyl-3-(p-methylphenyl)pyrazol-4-yl]acrylic acid. | β-[1-Phenyl-3-(p-methylphenyl)pyrazol-4-yl]propionic acid. |
| β-[1-Phenyl-3-(p-butylphenyl)pyrazol-4-yl]acrylic acid. | β-[1-Phenyl-3-(p-butylphenyl)pyrazol-4-yl]propionic acid. |
| β-[1-Phenyl-3-(p-methoxyphenyl)pyrazol-4-yl]acrylic acid. | β-[1-Phenyl-3-(p-methoxyphenyl)pyrazol-4-yl]propionic acid. |
| β-[1-Phenyl-3-(p-butoxyphenyl)pyrazol-4-yl]acrylic acid. | β-[1-Phenyl-3-(p-butoxyphenyl)pyrazol-4-yl]propionic acid. |
| β-[1-Phenyl-3-(3,4-dimethoxyphenyl)pyrazol-4-yl]acrylic acid. | β-[1-Phenyl-3-(3,4-dimethoxyphenyl)pyrazol-4-yl]propionic acid. |
| β-[1-Phenyl-3-(p-hydroxyphenyl)pyrazol-4-yl]acrylic acid. | β-[1-Phenyl-3-(p-hydroxyphenyl)pyrazol-4-yl]propionic acid. |
| β-[1-Phenyl-3-(p-nitrophenyl)pyrazol-4-yl]acrylic acid. | β-[1-Phenyl-3-(p-aminophenyl)pyrazol-4-yl]propionic acid. |
| β-[1-Phenyl-3-(p-dimethylaminophenyl)pyrazol-4-yl]acrylic acid. | β-[1-Phenyl-3-(p-dimethylaminophenyl)pyrazol-4-yl]propionic acid. |
| β-[1-Phenyl-3-(m-trifluoromethylphenyl)pyrazol-4-yl]acrylic acid. | β-[1-Phenyl-3-(m-trifluoromethylphenyl)pyrazol-4-yl]propionic acid. |
| β-[1-Phenyl-3-(p-methylthiophenyl)pyrazol-4-yl]acrylic acid. | β-[1-Phenyl-3-(p-methylthiophenyl)pyrazol-4-yl]propionic acid. |
| β-[1-Phenyl-3-(naphth-1-yl)-pyrazol-4-yl]acrylic acid. | β-[1-Phenyl-3-(naphth-1-yl)-pyrazol-4-yl]propionic acid. |
| β-[1-Phenyl-3-(naphth-2-yl)-pyrazol-4-yl]acrylic acid. | β-[1-Phenyl-3-(naphth-2-yl)-pyrazol-4-yl]propionic acid. |
| β-[1-Phenyl-3-(fur-2-yl)-pyrazol-4-yl]acrylic acid. | β-[1-Phenyl-3-(fur-2-yl)-pyrazol-4-yl]propionic acid. |
| β-[1-Phenyl-3-(fur-3-yl)-pyrazol-4-yl]acrylic acid. | β-[1-Phenyl-3-(fur-3-yl)-pyrazol-4-yl]propionic acid. |
| β-[1-Phenyl-3-(thien-2-yl)-pyrazol-4-yl]acrylic acid. | β-[1-Phenyl-3-(thien-2-yl)-pyrazol-4-yl]propionic acid. |
| β-[1-Phenyl-3-(thien-3-yl)-pyrazol-4-yl]acrylic acid. | β-[1-Phenyl-3-(thien-3-yl)-pyrazol-4-yl]propionic acid. |
| β-[1-Phenyl-3-(pyrid-2-yl)-pyrazol-4-yl]acrylic acid. | β-[1-Phenyl-3-(pyrid-2-yl)-pyrazol-4-yl]propionic acid. |
| β-[1-Phenyl-3-(pyrid-3-yl)-pyrazol-4-yl]acrylic acid. | β-[1-Phenyl-3-(pyrid-3-yl)-pyrazol-4-yl]propionic acid. |
| β-[1-Phenyl-3-(pyrid-4-yl)-pyrazol-4-yl]acrylic acid. | β-[1-Phenyl-3-(pyrid-4-yl)-pyrazol-4-yl]propionic acid. |
| β-[1-Phenyl-3-(indol-2-yl)-pyrazol-4-yl]acrylic acid. | β-[1-Phenyl-3-(indol-2-yl)-pyrazol-4-yl]propionic acid |
| β-[1-Phenyl-3-(indol-3-yl)-pyrazol-4-yl]acrylic acid. | β-[1-Phenyl-3-(indol-3-yl)-pyrazol-4-yl]propionic acid. |
| β-[1-Phenyl-3-(pyrrol-2-yl)-pyrazol-4-yl]acrylic acid. | β-[1-Phenyl-3-(pyrrol-2-yl)-pyrazol-4-yl]propionic acid. |

-continued

| Acrylic Acid. | Propionic Acid. |
|---|---|
| β-[1-Phenyl-3-(pyrrol-3-yl)-pyrazol-4-yl]acrylic acid. | β-[1-Phenyl-3-(pyrrol-3-yl)-pyrazol-4-yl]propionic acid. |

EXAMPLE 14

Following the procedure of Example 12, the following acrylic acid drivatives were reduced to the propionic acids indicated:

| Acrylic Acid. | Propionic Acid. |
|---|---|
| β-[3-Phenyl-1-(p-fluorophenyl)pyrazol-4-yl]acrylic acid. | β-[3-Phenyl-1-(p-fluorophenyl)pyrazol-4-yl]propionic acid. |
| β-[3-Phenyl-1-(p-bromophenyl)pyrazol-4-yl]acrylic acid. | β-[3-Phenyl-1-(p-bromophenyl)pyrazol-4-yl]propionic acid. |
| β-[3-Phenyl-1-(o-chlorophenyl)pyrazol-4-yl]acrylic acid. | β-[3-Phenyl-1-(o-chlorophenyl)pyrazol-4-yl]propionic acid. |
| β-[3-Phenyl-1-(o-methylphenyl)pyrazol-4-yl]acrylic acid. | β-[3-Phenyl-1-(o-methylphenyl)pyrazol-4-yl]propionic acid. |
| β-[3-Phenyl-1-(m-methylphenyl)pyrazol-4-yl]acrylic acid. | β-[3-Phenyl-1-(m-methylphenyl)pyrazol-4-yl]propionic acid. |
| β-[3-Phenyl-1-(p-methylphenyl)pyrazol-4-yl]acrylic acid. | β-[3-Phenyl-1-(p-methylphenyl)pyrazol-4-yl]propionic acid. |
| β-[3-Phenyl-1-(p-butylphenyl)pyrazol-4-yl]acrylic acid. | β-[3-Phenyl-1-(p-butylphenyl)pyrazol-4-yl]propionic acid. |
| β-[3-Phenyl-1-(p-methoxyphenyl)pyrazol-4-yl]acrylic acid. | β-[3-Phenyl-1-(p-methoxyphenyl)pyrazol-4-yl]propionic acid. |
| β-[3-Phenyl-1-(p-butoxyphenyl)pyrazol-4-yl]acrylic acid. | β-[3-Phenyl-1-(p-butoxyphenyl)pyrazol-4-yl]propionic acid. |
| β-[3-Phenyl-1-(3,4-dimethoxyphenyl)pyrazol-4-yl]acrylic acid. | β-[3-Phenyl-1-(3,4-dimethoxyphenyl)pyrazol-4-yl]propionic acid. |
| β-[3-Phenyl-1-(p-hydroxyphenyl)pyrazol-4-yl]acrylic acid. | β-[3-Phenyl-1-(p-hydroxyphenyl)pyrazol-4-yl]propionic acid. |
| β-[3-Phenyl-1-(p-nitrophenyl)pyrazol-4-yl]acrylic acid. | β-[3-Phenyl-1-(p-aminophenyl)pyrazol-4-yl]propionic acid. |
| β-[3-Phenyl-1-(p-dimethylaminophenyl)pyrazol-4-yl]acrylic acid. | β-[3-Phenyl-1-(p-dimethylaminophenyl)pyrazol-4-yl]propionic acid. |
| β-[3-Phenyl-1-(m-trifluoromethylphenyl)pyrazol-4-yl]acrylic acid. | β-[3-Phenyl-1-(m-trifluoromethylphenyl)pyrazol-4-yl]propionic acid. |
| β-[3-Phenyl-1-(p-methylthiophenyl)pyrazol-4-yl]acrylic acid. | β-[3-Phenyl-1-(p-methylthiophenyl)pyrazol-4-yl]propionic acid. |
| β-[3-Phenyl-1-(naphth-1-yl)pyrazol-4-yl]acrylic acid. | β-[3-Phenyl-1-(naphth-1-yl)pyrazol-4-yl]propionic acid. |
| β-[3-Phenyl-1-(naphth-2-yl)pyrazol-4-yl]acrylic acid. | β-[3-Phenyl-1-(naphth-2-yl)pyrazol-4-yl]propionic acid. |
| β-[3-Phenyl-1-(fur-2-yl)-pyrazol-4-yl]acrylic acid. | β-[3-Phenyl-1-(fur-2-yl)-pyrazol-4-yl]propionic acid. |
| β-[3-Phenyl-1-(fur-3-yl)-pyrazol-4-yl]acrylic acid. | β-[3-Phenyl-1-(fur-3-yl)-pyrazol-4-yl]propionic acid. |
| β-[3-Phenyl-1-(thien-2-yl)-pyrazol-4-yl]acrylic acid. | β-[3-Phenyl-1-(thien-2-yl)-pyrazol-4-yl]propionic acid. |
| β-[3-Phenyl-1-(thien-3-yl)-pyrazol-4-yl]acrylic acid. | β-[3-Phenyl-1-(thien-3-yl)-pyrazol-4-yl]propionic acid. |
| β-[3-Phenyl-1-(pyrid-2-yl)-pyrazol-4-yl]acrylic acid. | β-[3-Phenyl-1-(pyrid-2-yl)-pyrazol-4-yl]propionic acid. |
| β-[3-Phenyl-1-(pyrid-3-yl)-pyrazol-4-yl]acrylic acid. | β-[3-Phenyl-1-(pyrid-3-yl)-pyrazol-4-yl]propionic acid. |
| β-[3-Phenyl-1-(pyrid-4-yl)-pyrazol-4-yl]acrylic acid. | β-[3-Phenyl-1-(pyrid-4-yl)-pyrazol-4-yl]propionic acid. |
| β-[3-Phenyl-1-(indol-2-yl)-pyrazol-4-yl]acrylic acid. | β-[3-Phenyl-1-(indol-2-yl)-pyrazol-4-yl]propionic acid. |
| β-[3-Phenyl-1-(indol-3-yl)-pyrazol-4-yl]acrylic acid. | β-[3-Phenyl-1-(indol-3-yl)-pyrazol-4-yl]propionic acid. |
| β-[3-Phenyl-1-(pyrrol-2-yl)-pyrazol-4-yl]acrylic acid. | β-[3-Phenyl-1-(pyrrol-2-yl)-pyrazol-4-yl]propionic acid. |
| β-[3-Phenyl-1-(pyrrol-3-yl)-pyrazol-4-yl]acrylic acid. | β-[3-Phenyl-1-(pyrrol-3-yl)-pyrazol-4-yl]propionic acid. |

EXAMPLE 15

Following the procedure of Example 12, the following acrylic acid derivatives were reduced to the propionic acids indicated:

| Acrylic Acid. | Propionic Acid. |
|---|---|
| β-(1,3-Di-(p-chlorophenyl)-pyrazol-4-yl]acrylic acid. | β-[1,3-Di-(p-chlorophenyl)-pyrazol-4-yl]propionic acid. |
| β-[1-(p-Methylphenyl)-3-(p-chlorophenyl)pyrazol-4-yl]-acrylic acid. | β-[1-(p-Methylphenyl)-3-(p-chlorophenyl)pyrazol-4-yl]-propionic acid. |
| β-[1,3-Di-(p-methylphenyl)-pyrazol-4-yl]acrylic acid. | β-[1,3-Di-(p-methylphenyl)-pyrazol-4-yl]propionic acid. |
| β-[1,3-Di-(p-fluorophenyl)-pyrazol-4-yl]acrylic acid. | β-[1,3-Di-(p-fluorophenyl)-pyrazol-4-yl]propionic acid. |
| β-[1,3-Di-(p-bromophenyl)-pyrazol-4-yl]acrylic acid. | β-[1,3-Di-(p-bromophenyl)-pyrazol-4-yl]propionic acid. |
| β-[1,3-Di-(o-chlorophenyl)-pyrazol-4-yl]acrylic acid. | β-[1,3-Di-(o-chlorophenyl)-pyrazol-4-yl]propionic acid. |
| β-[1,3-Di-(o-methylphenyl)-pyrazol-4-yl]acrylic acid. | β-[1,3-Di-(o-methylphenyl-pyrazol-4-yl]propionic acid. |
| β-[1,3-Di-(m-methylphenyl)-pyrazol-4-yl]acrylic acid. | β-[1,3-Di-(m-methylphenyl)-pyrazol-4-yl]propionic acid. |
| β-[1,3-Di-(p-butylphenyl)-pyrazol-4-yl]acrylic acid. | β-[1,3-Di-(p-butylphenyl)-pyrazol-4-yl]propionic acid. |
| β-[1,3-Di-(p-methoxyphenyl)-pyrazol-4-yl]acrylic acid. | β-[1,3-Di-(p-methoxyphenyl)-pyrazol-4-yl]propionic acid. |
| β-[1,3-Di-(p-dimethylaminophenyl)pyrazol-4-yl]acrylic acid. | β-[1,3-Di-(p-dimethylaminophenyl)pyrazol-4-yl]propionic acid. |
| β-[1,3-Di-(m-trifluoromethylphenyl)pyrazol-4-yl]acrylic acid. | β-[1,3-Di-(m-trifluoromethylphenyl)pyrazol-4-yl]propionic acid. |

EXAMPLE 16

Ethyl 3-(p-chlorophenyl)-1-phenylpyrazol-4-ylacetate.

A solution of the acetic acid of Example 2 in saturated ethanolic hydrogen chloride was heated under reflux for 2 hours followed by evaporation to dryness. Recrystallisation of the residue gave the title ester.

EXAMPLE 17

Ethyl β-[3-(p-chlorophenyl)-1-phenylpyrazol-4-yl]acrylate.

A solution of the acrylic acid of Example 5 in saturated ethanolic hydrogen chloride was heated under reflux for 2 hours followed by evaporation to dryness. Recrystallisation of the residue gave the title ester.

Any of the acrylic acid derivatives of Examples 9, 10 and 11 could be converted to the corresponding ethyl ester in similar manner.

EXAMPLE 18

β-[3-(p-Chlorophenyl)-1-phenylpyrazol-4-yl]acrylohydroxamic acid.

A solution of hydroxylamine hydrochloride in methyl alcohol was added to a stirred solution of 1 equivalent of sodium in methyl alcohol. The mixture was placed in a refrigerator for 1.5 hours, the sodium chloride removed by filtration and the filtrate added to a stirred solution of the ester of Example 17 in methyl alcohol. After 16 hours at room temperature, the mixture was poured into a dilute solution of hydrochloric acid to precipitate the title compound.

EXAMPLE 19

γ-[3-(p-Chlorophenyl)-1-phenylpyrazol-4-yl]butyric acid.

The acid of Example 2 was reduced with lithium aluminium hydride in the usual manner to give the corresponding 3-(p-chlorophenyl)-1-phenyl-4-hydroxyethylpyrazole. Chlorination with thionyl chloride gave the corresponding chloroethyl compound which was reacted with diethyl sodiomalonate in the normal manner to give 3-(p-chlorophenyl)-1-phenyl-4-(3'-(diethoxycarbonyl) propyl]pyrazole. The usual hydrolysis and concomitant decarboxylation afforded the title compound.

In the pharmacological evaluation of the properties of the compounds of this invention, the effects in vivo of the compounds are tested in the procedure of Winter et al in Proc. Soc. Biol. Med, 111, 544 (1962) and Buttle et al in Nature, 179, 629 (1957).

The compounds of general formula I when administered orally in the above test procedures at a dosage of 3 to 250 mg./Kg. depending on the compound in question demonstate anti-inflammatory activity.

EXAMPLE 20

| | |
|---|---|
| 3-(p-Chlorophenyl)-1-phenylpyrazol-4-ylacetic acid | 125 mg. |
| Lactose | 120 mg. |
| Magnesium stearate | 5 mg. |

Capsules of the above were made up by thoroughly mixing together batches of the above ingredients and filling hard gelatine capsules (250 mg.) with the mixture.

EXAMPLE 21

| | |
|---|---|
| 3-(p-Chlorophenyl)-1-(m-methylphenyl)pyrazol-4-ylacetic acid | 125 mg. |
| Lactose | 100 mg. |

-continued

| | |
|---|---|
| Avicel | 30 mg. |
| Dried Maize Starch | 40 mg. |
| Magnesium Stearate | 5 mg. |

Tablets of the above composition were made by milling the active ingredient to 40 mesh (British Standard), sieving through a 40 mesh (British Standard) sieve, mixing the milled material with the other components and compressing to form tablets.

What is claimed is:

1. A compound having the formula

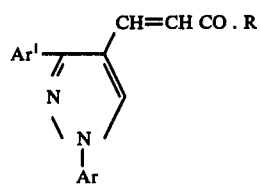

in which Ar and Ar¹ are aryl radicals selected from the group consisting of phenyl, halophenyl, lower alkyl phenyl, lower alkoxyphenyl, dimethoxyphenyl, hydroxyphenyl, nitrophenyl, di-(lower alkyl)aminophenyl, trifluoromethylphenyl, methylthiophenyl, furyl, thienyl and pyrryl with the proviso that at least one of Ar and Ar¹ is phenyl or substituted phenyl; and R is a member of the group consisting of hydroxy, lower alkoxy and amido.

2. A compound according to claim 1 which is β-[3-(p-chlorophenyl-1-phenylpyrazol-4-yl] acrylic acid.

* * * * *